United States Patent
Hiruma et al.

(10) Patent No.: US 8,241,238 B2
(45) Date of Patent: Aug. 14, 2012

(54) CELL SELECTION APPARATUS

(75) Inventors: Teruo Hiruma, Hamamatsu (JP);
Hidenao Iwai, Hamamatsu (JP);
Susumu Terakawa, Hamamatsu (JP)

(73) Assignees: Hamamatsu Photonics K.K.,
Hamamatsu-shi, Shizuoka (JP); National University Corporation Hamamatsu University School of Medicine,
Hamamatsu-shi, Shizuoka (JP)

( * ) Notice: Subject to any disclaimer, the term of this patent is extended or adjusted under 35 U.S.C. 154(b) by 646 days.

(21) Appl. No.: 12/301,483

(22) PCT Filed: May 15, 2007

(86) PCT No.: PCT/JP2007/059949
§ 371 (c)(1),
(2), (4) Date: Feb. 2, 2009

(87) PCT Pub. No.: WO2007/135896
PCT Pub. Date: Nov. 29, 2007

(65) Prior Publication Data
US 2009/0198168 A1  Aug. 6, 2009

(30) Foreign Application Priority Data
May 22, 2006  (JP) .............................. P2006-141796

(51) Int. Cl.
*A61M 37/00* (2006.01)
*A61M 1/00* (2006.01)
*B01D 11/00* (2006.01)
*B01D 61/00* (2006.01)
*C02F 1/00* (2006.01)
*C02F 1/34* (2006.01)
*C02F 1/48* (2006.01)
*G06K 9/00* (2006.01)

(52) U.S. Cl. ...................... 604/6.08; 604/4.01; 604/5.01; 422/44; 210/645; 210/748.01; 382/133

(58) Field of Classification Search ................ 604/5.02, 604/5.04, 6.01, 6.02, 6.03, 6.06, 6.08, 6.09, 604/6.16, 20; 600/309, 368, 481, 573; 209/3, 209/10, 12.1, 132, 422
See application file for complete search history.

(56) References Cited

U.S. PATENT DOCUMENTS
4,315,514 A * 2/1982 Drewes et al. ................ 600/427
(Continued)

FOREIGN PATENT DOCUMENTS
JP  S57-500995  6/1982
(Continued)

OTHER PUBLICATIONS

M. Cristofanilli et al., "Circulating Tumor Cells, Disease Progression, and Survival in Metastatic Breast Cancer," The New England Journal of Medicine, Aug. 19, 2004, pp. 781-791, vol. 351, No. 8.
(Continued)

*Primary Examiner* — Leslie Deak
*Assistant Examiner* — Adam Marcetich
(74) *Attorney, Agent, or Firm* — Drinker Biddle & Reath LLP

(57) ABSTRACT

A cell sorting apparatus includes an extracorporeal circulation system 10 for sampling blood from a subject and circulating the blood outside a body; a cell measuring section 20 for supplying measurement light to cells contained in the blood to optically measure cell information on the physical quantity relating to the volume of the cell itself or a nucleus of the cell; and a cell separating section 30 for separating cells with reference to the cell information measured. The cell separating section 30 separates cells, based on the cell information measured by the cell measuring section 20 and a sorting condition set for sorting a specific type of cell such as a cancer cell, the cells satisfying the sorting condition, and returns the other cells into the body via the extracorporeal circulation system 10. Thus, a cell sorting apparatus can be realized which is capable of suitably sorting a target cell from the cells in blood.

6 Claims, 6 Drawing Sheets

U.S. PATENT DOCUMENTS

| | | | | |
|---|---|---|---|---|
| 5,434,081 | A * | 7/1995 | Maekawa | 436/17 |
| 5,538,724 | A * | 7/1996 | Butcher et al. | 424/152.1 |
| 5,948,272 | A * | 9/1999 | Lemelson | 210/745 |
| 5,995,645 | A * | 11/1999 | Soenksen et al. | 382/133 |
| 6,589,792 | B1 * | 7/2003 | Malachowski | 436/63 |
| 6,636,623 | B2 * | 10/2003 | Nelson et al. | 382/133 |
| 6,727,071 | B1 * | 4/2004 | Dunlay et al. | 435/7.21 |
| 7,491,502 | B2 * | 2/2009 | Lin | 435/7.21 |
| 2002/0164063 | A1 * | 11/2002 | Heckman | 382/133 |
| 2002/0188240 | A1 * | 12/2002 | Gorsuch | 604/6.04 |
| 2003/0044832 | A1 * | 3/2003 | Blankenstein | 435/6 |
| 2004/0057037 | A1 * | 3/2004 | Ohishi et al. | 356/39 |
| 2004/0081345 | A1 * | 4/2004 | Douglass | 382/133 |
| 2005/0057756 | A1 * | 3/2005 | Fang-Yen et al. | 356/497 |
| 2005/0105097 | A1 * | 5/2005 | Fang-Yen et al. | 356/497 |
| 2005/0164158 | A1 * | 7/2005 | Wang et al. | 435/2 |
| 2005/0167621 | A1 * | 8/2005 | Zeng et al. | 250/580 |
| 2005/0202400 | A1 * | 9/2005 | Tsuji et al. | 435/4 |
| 2005/0207940 | A1 * | 9/2005 | Butler et al. | 422/73 |
| 2006/0141628 | A1 * | 6/2006 | Evans | 436/63 |
| 2006/0186061 | A1 * | 8/2006 | Briggs et al. | 210/787 |
| 2006/0204071 | A1 * | 9/2006 | Ortyn et al. | 382/133 |
| 2006/0268260 | A1 * | 11/2006 | Liu et al. | 356/72 |

FOREIGN PATENT DOCUMENTS

| | | |
|---|---|---|
| JP | 6-61360 | 8/1994 |
| JP | 7-3419 | 1/1995 |
| JP | 7-270302 | 10/1995 |
| JP | 2003-250882 | 9/2003 |
| JP | 2005-515781 | 6/2005 |
| WO | 03/064632 | 8/2003 |

OTHER PUBLICATIONS

A. Hirai et al., "Laser Photophoresis of a Single Droplet in Oil in Water Emulsions," Langmuir, 1996, pp. 5570-5575, vol. 12, No. 23, American Chemical Society.

A. Dunn et al., "Finite-Difference Time-Domain Simulation of Light Scattering from Single Cells," Journal of Biomedical Optics, Jul. 1997, pp. 262-266, vol. 2, No. 3.

T. Tanaka et al., "Chemokines in tumor progression and metastasis," Cancer Sci., Jun. 2005, pp. 317-322, vol. 96, No. 6.

A. Müller, "Involvement of chemokine receptors in breast cancer metastasis," Nature, Mar. 2001, pp. 50-56, vol. 410.

K. Creath, "Phase-Measurement Interferometry Techniques," E. Wolf, Progress in Optics XXVI, 1988, pp. 349-393, Elsevier Science Publishers B.V.

Y. Zhao et al., "Phase-resolved optical coherence tomography and optical Doppler tomography for imaging blood flow in human skin with fast scanning speed and high velocity sensitivity," Optics Letters, Jan. 15, 2000, pp. 114-116, vol. 25, No. 2.

J. Leary, "Strategies for Rare Cell Detection and Isolation," Methods in Cell Biology, 1994, pp. 331-358, vol. 42.

M. P. MacDonald et al., "Microfluidic sorting in an optical lattice," Nature, Nov. 27, 2003, pp. 421-424, vol. 426.

* cited by examiner

CELL SELECTION APPARATUS

TECHNICAL FIELD

The present invention relates to a cell sorting apparatus for sorting a specific type of cell from cells in blood.

BACKGROUND ART

A treating method for metastatic cancers and details of a metastasis mechanism of a cancer are still unresolved problems. For example, although it is known a cancer cell metastasizes to another organ through a blood vessel, a detailed mechanism for this is unresolved. There is a possibility that a method for, for example, specifying the cancer cells in blood and counting the number of cancer cells can be used for prediction of convalescence of a cancer, evaluation of a treatment effect or the like (for example, see "The New England Journal of Medicine Vol. 351, pp. 781-791 (2004)"). Additionally, it is estimated that removal of cancer cells in blood allows a metastasis probability to be lowered. Regarding handling of such cancer cells in blood, for example, patent document 1: Japanese Patent Publication No. H6-61360 and document 2: Japanese Patent Publication No. H7-3419 disclose analysis of cells in blood.

Patent Document 1: Japanese Patent Publication No. H6-61360

Patent Document 2: Japanese Patent Publication No. H7-3419

DISCLOSURE OF THE INVENTION

Problems to be Solved by the Invention

Regarding the above described analysis of cells, it is thought that acquiring an image of a cell in blood sampled from a subject and then showing the image to a doctor or researcher is useful for establishment of a treating and diagnosing method for metastatic cancers or solution of a metastasis mechanism. However, in the case of acquiring images of all the cells in blood, there arise problems such as an increase in memory size necessary for recording images, and an increase in time for acquiring images or processing images. For solving such problems, it is necessary to sort a target cell such as a cancer cell or abnormal cell from the cells in blood.

On the other hand, the above patent document 1 discloses that, for sorting cells causing a specific disease, marks are applied to the cells with use of a marking material such as a fluorescent antibody, DNA sonde or RNA sonde. However, in the method for applying the marks to the cells, there is a possibility that the used marking material is also returned into a body of the subject in the case of returning normal cells other than the cells causing the specific disease into the body. When such an excess marking material returns into the body of the subject, the material sometimes causes damage to the normal cells and the like of the subject. Additionally, although the patent document 1 discloses destruction or inactivation of cells, there is, in this case, a possibility that the remaining destroyed cells are also returned into the body.

The present invention was made to solve the above problems, and it is an object of the present invention to provide a cell sorting apparatus capable of suitably sorting a target cell from cells in blood.

Means for Solving the Problem

In order to achieve the object, the cell sorting apparatus of the present invention includes: (1) an extracorporeal circulation system for sampling blood from a subject, circulating the blood outside a body and returning the blood into the body; (2) cell measuring means for supplying measurement light to cells contained in the blood sampled by the extracorporeal circulation system to optically measure cell information on the physical quantity relating to the volume of the cell itself or a nucleus of the cell; and (3) cell separating means for separating, based on the cell information measured by the cell measuring means and a sorting condition set for sorting a specific type of cell, cells which satisfy the sorting condition, and returning the other cells into the body via the extracorporeal circulation system.

In the above-described cell sorter, the measurement light is applied to the cells in the blood sampled by the extracorporeal circulation system, and information on the physical quantity relating to the volume of the cell or the physical quantity relating to the volume of the nucleus of the cell is acquired. The cell information relating to the volume is thus acquired with the optical measuring method, and thus, even in the case of returning the normal cells to the body of the subject, the subject is prevented from being damaged. Additionally, in such a method, a process for sorting a specific type of cell (e.g. cancer cell) can be simplified and shortened.

Additionally, a predetermined sorting condition is applied to the cell information acquired with the optical measuring method, and the cells, each of which cell information is measured, are separated into a cell group having a possibility of containing a target cell, and a normal cell group containing the other cells to be returned into the body. Thus, the cells in the blood can be suitably sorted without addition of an excess material, etc. Here, the above-described physical quantity relating to the volume indicates the physical quantity relating to the size of the cell or nucleus thereof occupying a space, and includes, for example, thickness in addition to the volume itself. Additionally, single means may be used that realizes both functions of the cell measuring means and cell separating means.

Effect of the Invention

According to a cell sorting apparatus of the present invention, information of cells in blood sampled by an extracorporeal circulation system is acquired with an optical measuring method, the information regarding the physical quantity relating to the volume of the cell or a nucleus of the cell, a predetermined sorting condition is applied to the acquired cell information, the cells, each of which cell information is measured, are separated into a cell group having a possibility of containing a target cell, and a normal cell group containing the other cells to be returned into a body, and thus the target cell can be suitably sorted from the cells in the blood.

DESCRIPTION OF THE SYMBOLS

10—Extracorporeal circulation system, 11—Main circulation system, 12—Sorting circulation system (bypass circulation system), 13—Pre-sorting section, 14—Supplying section, 15—Flow path system, 16—Input flow path, 17—Flow cell, 18—Output flow path, 20—Cell measuring section, 21—Measuring section, 22—Measurement light source, 23—Detector, 25—Separation instructing unit, 30—Cell separating section, 31—Input flow path, 32—First output flow path, 33—Second output flow path, 35—Separating valve, 40—Image acquiring section, 41—Imaging section, 42—Imaging device, 45—Image analyzer, 46—Display, 50—Cell treating section, 60—Interference optical system, 61, 66—Half mirror, 62, 65—Galvano mirror, 63, 64—Telecentric fθ lens, L0—Measurement light, L1—Irradiation light, L2—Reference light, L3—Interference light.

BEST MODES FOR CARRYING OUT THE INVENTION

Hereinafter, preferable embodiments of a cell sorting apparatus according to the present invention will be described in detail with reference to the drawings. Moreover, in descriptions of the drawings, the same reference symbol is attached to the same element, and an overlapping description thereof will be omitted. Additionally, the dimensional proportions of the drawings do not always correspond to that described.

Figure 1:
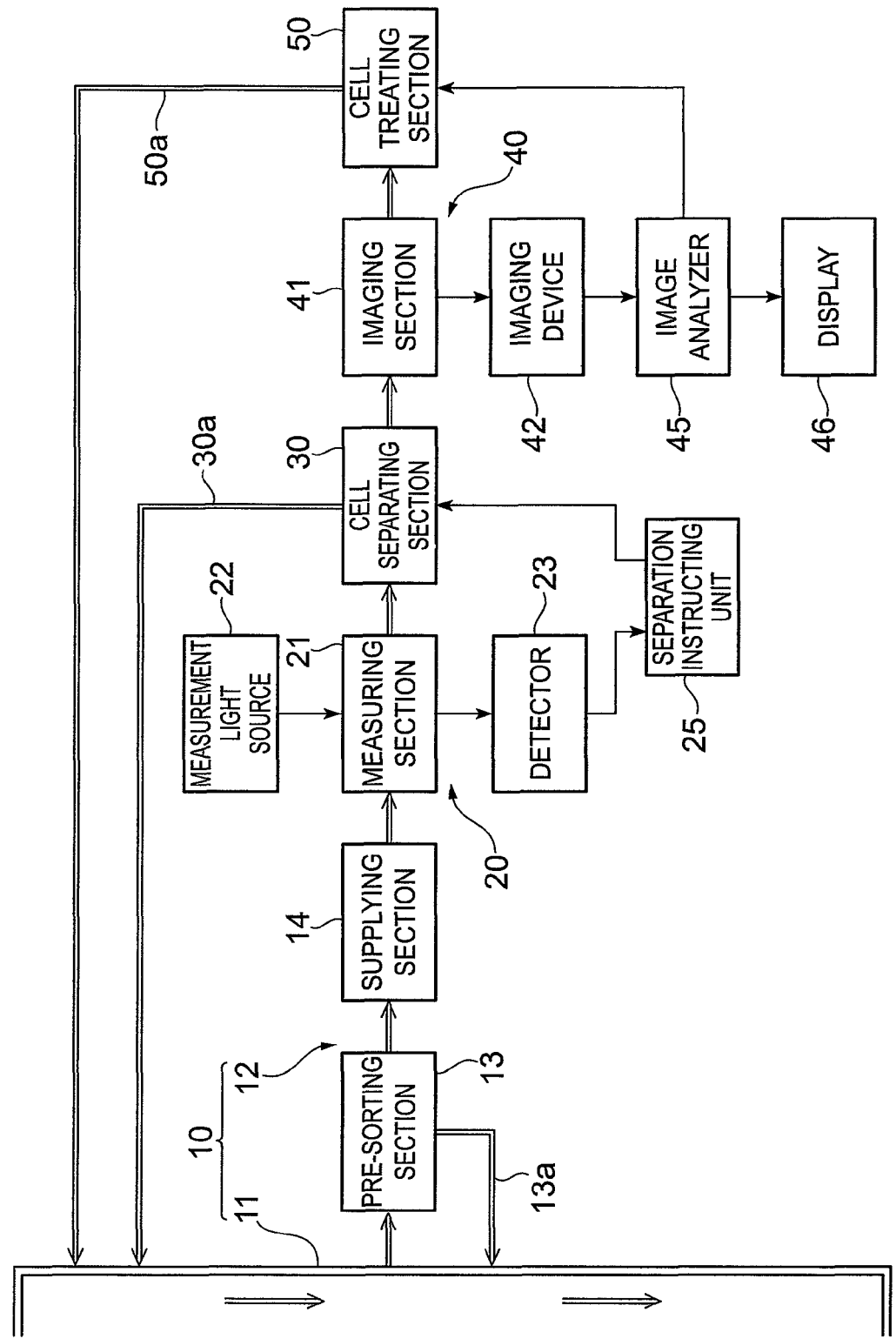
FIG. 1 is a block diagram schematically illustrating a constitution of a cell sorting apparatus of an embodiment.

FIG. 1 is a block diagram schematically illustrating a configuration of the cell sorting apparatus of an embodiment of the present invention. The cell sorting apparatus sorts a specific type of cell from cells in blood sampled from a subject, and includes an extracorporeal circulation system 10, a cell measuring section 20, a cell separating section 30, an image acquiring section 40 and a cell treating section 50. Moreover, hereinafter, the subject will indicate a body of a patient, the case of sorting a cancer cell as a specific type of cell will be mainly exemplified, and cell sorting by the apparatus will be described.

The extracorporeal circulation system 10 is a circulation flow path system for sampling blood from the subject, circulating it outside a body, and returning it into the body. In this embodiment, the extracorporeal circulation system 10 has a main circulation system 11 in which the blood sampled from the subject flows and returns into the body, and a sorting circulation system 12 which is provided as a bypass circulation system to the main circulation system 11 and used for cell sorting.

In the sorting circulation system 12, a pre-sorting section 13, a supplying section 14, a measuring section 21 and a cell separating section 30 are provided in this order from the upstream side. The pre-sorting section 13 classifies, as pre-sorting for cells in blood, cells to be measured into a cell group containing erythrocytes and a cell group containing leukocytes. Here, the cancer cell, which is the specific type of cell, is sorted as the cell group containing leukocytes. Accordingly, in this case, the cells sorted as the cell group containing leukocytes are transmitted to the supplying section 14 of the subsequent stage in the sorting circulation system 12. Additionally, the cells sorted as the cell group containing erythrocytes are returned to the main circulation system 11 via a flow path 13a.

As such a method for pre-sorting the cells, specifically, for example, a centrifugal separation method can be adopted. Additionally, as a separator, for example, COBE Spectra made by GAMBRO. BCT, Inc., Baxter Amicus Separator made by Baxter, Inc., each of which is a blood component separator, and the like are cited. Alternatively, a method for separating cells may be used by applying a light scattering force or light gradient force (for example, see "A. Hirai, H. Monjushiro, and H. Watarai, "Laser-Photophoresis of a Single Droplet in o/w Emulsions", Langmuir 12, pp. 5570-5575 (1997)").

The supplying section 14 controls a flow of blood so as to supply blood containing cells to the measuring section 21 under a suitable condition for measurement of cells. Here, the suitable condition for measurement of cells indicates, for example, a blood supply condition that, when the measuring section 21 of the subsequent stage measures the cells while scanning the flow of blood, the plurality of cells do not overlap with each other when viewed from a scanning surface. As the supplying section 14, for example, a specially designed flow path may be used such as a flow path disclosed in Japanese Translation of PCT International Application No. S57-500995. Additionally, a laminar flow may be made by a sheath flow used in a common flow cytometer so that cells are supplied one by one.

The measuring section 21 constitutes the cell measuring section 20 in the sorting apparatus together with a measurement light source 22 and detector 23. The cell measuring section 20 is measuring means for supplying measurement light to cells in blood sampled by the extracorporeal circulation system 10 for optically measuring cell information on the physical quantity relating to the volume of the cell itself or a nucleus of the cell.

In the constitution illustrated in FIG. 1, firstly, blood flowing through the flow path in the measuring section 21 is irradiated with the measurement light supplied from the measurement light source 22 so that blood is scanned. Then, light from the cell passing through a predetermined region of the blood, which is irradiated with the measurement light, is detected by the detector 23 so that the cell information on the physical quantity relating to the volume of the cell or nucleus of the cell is acquired. Here, as the light emitted from a cell to be detected by the detector 23, specifically, for example, fluorescence, reflected light, scattered light, transmitted light and the like from the cell can be used, and the optical characteristic of the cell is extracted based on the light.

Figure 2:
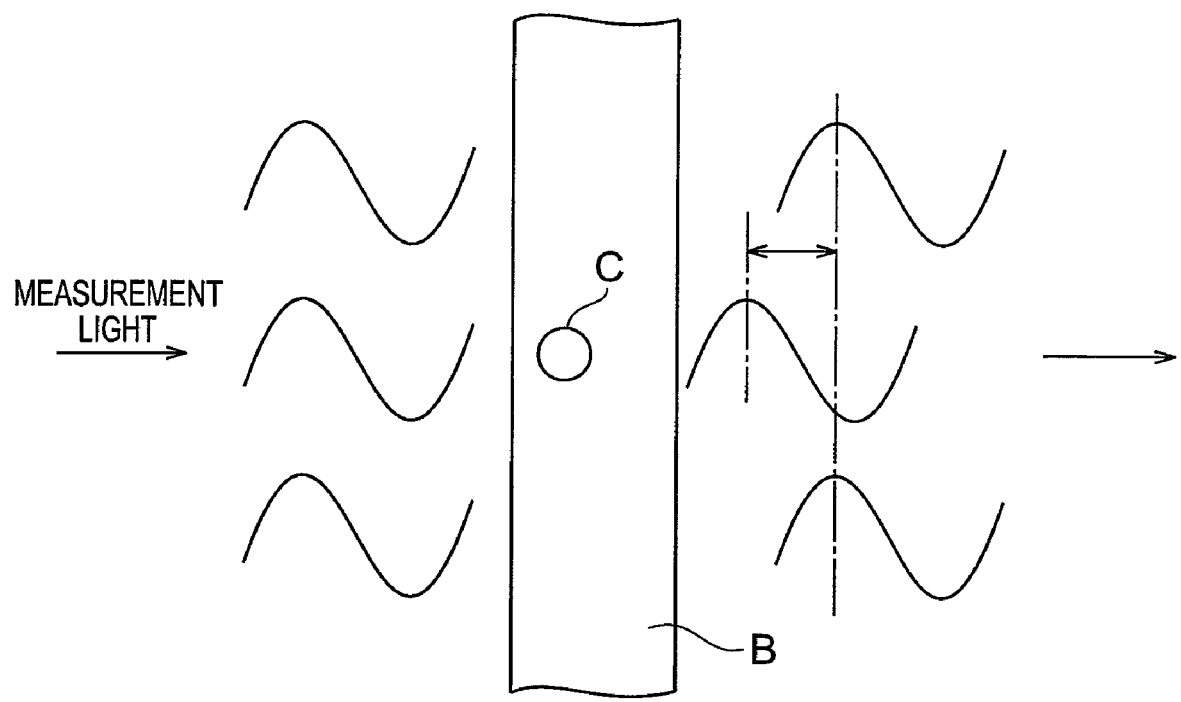
FIG. 2 is a diagram illustrating an example of a method for acquiring cell information in a cell measuring section.

FIG. 2 is a diagram illustrating an example of a method for acquiring the cell information in the cell measuring section 20. In the example illustrated in FIG. 2, a method is used, the method of irradiating a predetermined region of blood B containing a cell C in the measuring section 21 with the measurement light supplied from the measurement light source 22 to set phase difference information, which is acquired by detecting light passing through the cell C, as the cell information.

In this method, as a phase change of the measurement light schematically illustrated in FIG. 2, phase difference is generated between the light passing through only the blood B and light passing through the cell C, based on a refractive index difference between the blood B and the cell C, and delay of the light caused by the refractive index difference. Additionally, the distance that the measurement light passes through the cell C depends on the volume, thickness or the like of the cell or nucleus of the cell. Accordingly, by detecting the light passing through the cell C and acquiring the phase difference information, information regarding the physical quantity relating to the volume of the cell or nucleus of the cell can be acquired, the information being necessary for sorting the cells.

The blood containing the cells, each of which the cell information is measured in the measuring section 21, is introduced into the cell separating section 30. The cell separating section 30 sorts and separates the cells based on the cell information measured in the cell measuring section 20 and a sorting condition set for sorting a specific type of cell (for example, cancer cell).

Specifically, in the case where the cell satisfies the sorting condition, that is, the case where the cell has a possibility of being the specific type of cell, the cell separating section 30 separates the cell (target cell). The separated cells are transmitted to an imaging section 41 of the subsequent stage. On the other hand, cells (non-target cell) other than the cells satisfying the sorting condition are returned to the main circulation system 11 as a non-specific type of cell via a flow path 30a. Thus, the cells, which do not satisfy the sorting condition, are returned into the body of the subject via the extracorporeal circulation system 10.

Additionally, in this embodiment, detection result information by the detector 23 is input into a separation instructing unit 25, the information being acquired as the cell information in the cell measuring section 20. Further, the sorting condition set for sorting a specific type of cell described above is previously stored in the separation instructing unit 25. The separation instructing unit 25 compares the cell information measured by the cell measuring section 20 with the sorting condition, and transmits, based on the result of comparison, a separation instructing signal indicating whether the cell satisfies the sorting condition.

The separation instructing signal is input into the cell separating section 30, and the cell separating section 30 separates and sorts the cells in accordance with the instruction of the separation instructing signal. As the separation instructing signal, for example, a trigger signal can be used that instructs separation of the cell in the case where the cell satisfies the sorting condition. Alternatively, a signal having a separation action of the cell by itself may be used as the separation instructing signal. As a signal having the separation action, for example, a beam signal, electric field and the like are cited, the beam signal having light scattering force or light gradient force as an optical tweezers, the electric field deviating liquid drops used in the cell sorter.

Moreover, it is preferable that the separation instructing signal is transmitted from the separation instructing unit 25 to the cell separating section 30 in consideration of the time when the cell reaches the cell separating section 30 from the measuring section 21. Additionally, as a cell group having a possibility of containing a specific type of cell to be separated in the cell separating section 30, both the cell group containing only a specific type of cell and the cell group containing the specific type of cell and others are applicable. As the cell group containing the specific type of cell and others, for example, a cell group containing cancer cells and many leukocyte cells existing around them is cited.

The cells, which are separated as cells having a possibility of being the specific type of cell in the cell separating section 30, are introduced into the imaging section 41. The imaging section 41 constitutes an image acquiring section 40 of the sorting apparatus together with an imaging device 42. The image acquiring section 40 is acquiring means for acquiring an image of the cell which is separated by the cell separating section 30 as a cell satisfying the sorting condition. Here, proper illumination light is applied to the cell in the imaging section 41, the cell is imaged by the imaging device 42 such as a CCD camera with lens, and thus image data of the cell is acquired. Additionally, the image data of the cell is acquired with a microscope or the like as the need arises.

The cell image data acquired by the imaging device 42 is input into an image analyzer 45. The image analyzer 45, for example, includes a computer, and serves as image storing means for recording and storing the image data in a memory, and as image analyzing means for performing necessary analysis to the image data. Additionally, a display 46 is connected to the image analyzer 45. The display 46 is displaying means for displaying the cell image acquired in the image acquiring section 40 to an operator.

The image analyzer 45, in the case of displaying the cell image to the operator, selects necessary data from the stored image data and transmits it to the display 46 to display the image. In this case, the operator can decide, with reference to the displayed cell image, whether the cell is the specific type of cell.

Additionally, the image analyzer 45 analyzes the cell image with a predetermined analyzing method as the need arises. Specifically, the information relating to the specific type of cell to be sorted is previously prepared in the image analyzer 45. The image analyzer 45, with reference to the information relating to the specific type of cell, analyzes the cell image and decides whether the cell is the specific type of cell.

The cells, each of which the image is acquired in the imaging section 41, are introduced into the cell treating section 50. The cell treating section 50, with reference to manual decision by the operator or automatic decision by the image analyzer 45, subjects the cells, which are decided as the specific type of cell, to a predetermined treatment, destroying, marking, detoxifying of the cell or the like, according to need. Additionally, as the need further arises, the cells, which are introduced into the cell treating section 50 and treated, are returned to the main circulation system 11 via a flow path 50a. In this case, the cells subjected to the predetermined treatment are returned into the body of the subject via the extracorporeal circulation system 10. Additionally, the cells not treated are not returned to the extracorporeal circulation system 10 and are dumped.

The effect of the cell sorting apparatus of the above embodiment will be described.

In the cell sorter illustrated in FIG. 1, in the cell measuring section 20, with use of the measurement light supplied from the measurement light source 22, information of the cell in blood sampled by the extracorporeal circulation system 10 is acquired, the information on the physical quantity relating to the volume of the cell or nucleus of the cell. The cell information is thus acquired by an optical measurement method, and thus, for example, an excess material such as a marking material is not required to be added to blood, and therefore, even if normal cells are returned into the body of the subject, it is prevented from causing damage to the subject. Here, the physical quantity relating to the volume of the cell or nucleus of the cell is the physical quantity relating to the size of the cell or nucleus of the cell occupying a space, and includes thickness and the like in addition to volume itself.

Additionally, the sorting condition set in accordance with characteristics or the like of the target specific type of cell is applied to the cell information acquired with the optical measurement method, and the cell separating section 30 separates the cells, each of which the cell information is measured, into the cell group having a possibility of containing the target cell, and the normal cell group containing the other cells to be returned into the body. Thus, the cells in blood can be suitably sorted. Additionally, in such a method, compared with a method for acquiring images of all the cells in blood and sorting the target cell, a specific type of cell such as a cancer cell can be simply and speedily sorted.

Specifically, assuming that a specific type of cell to be sorted is a cancer cell, a leukocyte infected with a cancer has a size (volume) about several to ten times as that of a normal leukocyte, optical characteristics of the normal cell and the leukocyte infected with the cancer are different from each other, the optical characteristic regarding, for example, an optical path length in the case where light passes. Accordingly, the cancer cells can be sorted by optically measuring the information regarding the volume, thickness or the like of the cell or nucleus of the cell by, for example, measurement of the phase difference information, as described above. Additionally, it is generally well known that a nucleus of a cancerous cell is hypertrophied, and forward scattered light depends on the scale of the nucleus (for example, see "A. Dunn, J. Biomed. Optics Vol. 2, pp. 262-266 (1997)"). Accordingly, with use of this, the cancer cell and normal cell may be distinguished from each other based on scattering intensity information of light.

Regarding measurement of the physical quantity relating to the volume of the cell or nucleus of the cell in the cell measuring section 20, various measuring methods are applicable, however, it is preferable to adopt a method for, as described above, irradiating a predetermined region of the blood containing the cell with the measurement light, detecting the light passing through the cell, and acquiring the phase difference information. The phase difference information generated when the measurement light passes through the cell is thus measured, and thus the cell information necessary for sorting the cells can be suitably acquired without addition of an excess material or the like. Additionally, such phase difference information, as described below, can be measured with use of, for example, an interference optical system.

Additionally, in the above embodiment, the separation instructing unit 25 is provided for the cell measuring section 20 and cell separating section 30, the unit comparing the measured cell information with the sorting condition, and transmitting the separation instructing signal based on the comparison result. Thus, the cells can be securely sorted and separated based on the cell information and sorting condition. Additionally, in this case, as the separation instructing signal, various types of signals can be used specifically as described above.

Additionally, in the cell sorting apparatus of the embodiment, in addition to the cell measuring section 20 and cell separating section 30, the image acquiring section 40 is further provided for acquiring the image of the cell which is separated by the cell separating section 30 as a cell satisfying the sorting condition. Such a constitution is effective for, for example, the case where the precision of cell sorting performed in the cell separating section 30 is desired to be raised.

That is, according to such a constitution, a first step of cell sorting is performed with use of the cell information measured by the cell measuring section 20, a second step of sorting is then performed with use of the image acquired by the image acquiring section 40, and the cells can be sorted at high precision. Additionally, since only the cells sorted at the first step and separated by the cell separating section 30 become a target of image acquiring, the memory size necessary for recording the images, and time necessary for acquiring images or processing images can be prevented from increasing, compared with the case where images of all the cells are acquired.

Specifically, it is considered that, for example, about $10^7$ cells are filtered to about $10^3$ cells by rough sorting in the cell measuring section 20 and cell separating section 30. Then, by setting the filtered cell group as a population, the images are acquired in the image acquiring section 40, or further the analysis and sorting for the cells are performed with use of the acquired images.

Additionally, according to the above constitution, the cell sorting by the cell measuring section 20 and cell separating section 30 can be performed in parallel with the image acquiring of the image acquiring section 40. In this case, the degree of freedom of cell sorting is raised, for example, the measurement in the cell measuring section 20 can be performed at high speed, and the image acquiring in the image acquiring section 40 of the subsequent stage can be performed at high resolution and slightly low speed. However, in the case where, for example, the sorting precision in the cell measuring section 20 and cell separating section 30 is sufficiently high, the image acquiring section 40 of the subsequent stage may not be provided, if it is not necessary.

Additionally, in the present embodiment, the display 46 is provided for displaying the cell image acquired by the image acquiring section 40. According to the constitution, the image displayed on the display 46 allows the operator (for example, a doctor) to decide, by visual recognition or the like, whether the cell is a specific type of cell (for example, a cancer cell).

Additionally, a constitution is applicable that the image analyzer 45 is provided for the image acquiring section 40, and analyzes the cell image acquired by the image acquiring section 40 with reference to previously prepared information of a specific type of cell to decide whether the cell is the specific type of cell. In such a constitution, the cell image is analyzed so that the cell can be automatically decided whether being a specific type of cell. As a specific analyzing method in this case, for example, a method is cited, the method for, in the case where the specific type of cell is a cancer cell, subjecting a pattern of a cancer cell, the pattern being pre-stored, and an acquired image pattern of the cell to pattern matching processing to distinguish the cancer cells and other cells from each other in accordance with a result of the matching processing.

Additionally, since the cells are previously sorted in the cell measuring section 20 and cell separating section 30 of the previous stage, in both cases where the operator manually carries out a decision on the cell, and the image analyzer 45 automatically carries out a decision on the cell, the number of cells necessary to be decided is reduced and the decision work is greatly reduced.

Additionally, in the cell sorting apparatus of the present embodiment, the cell treating section 50 is further provided at the subsequent stage of the cell measuring section 20, cell separating section 30 and image acquiring section 40, and the treated cells are returned into the body via the extracorporeal circulation system 10 as the need arises. According to such a constitution, various cell treatments can be realized, for example, with use of the fact that the cancer cell selectively metastasizes to a specific tissue, a medicine is selectively injected into a metastasis cancer focus so that the effect of medicine treatment is improved.

Additionally, in the case where there exists a cancer cell not expressing a function of thus selectively metastasizing to a specific tissue, it is preferable to subject the cancer cell to treatment for expressing a receptor causing homing (homing treatment). Generally, it is preferable that the cell treating section 50 subjects the cell to the homing treatment for expressing a homing function of directing the cell to a specific tissue. In this case, for example, a cell having the expressed homing function can be used as a conveyer of a medicine or the like. Additionally, regarding the homing, for example, it is possible to refer to the following documents: "T. Tanaka et al., "Chemokines and tumor invasion/metastasis" section in "Chemokines in tumor progression and metastasis", Cancer Sci. Vol. 96, pp. 317-322 (2005)"; and "A. Muller et al., "Involvement of chemokine receptors in breast cancer metastasis", Nature Vol. 410, pp. 50-56 (2001)".

Figure 3:
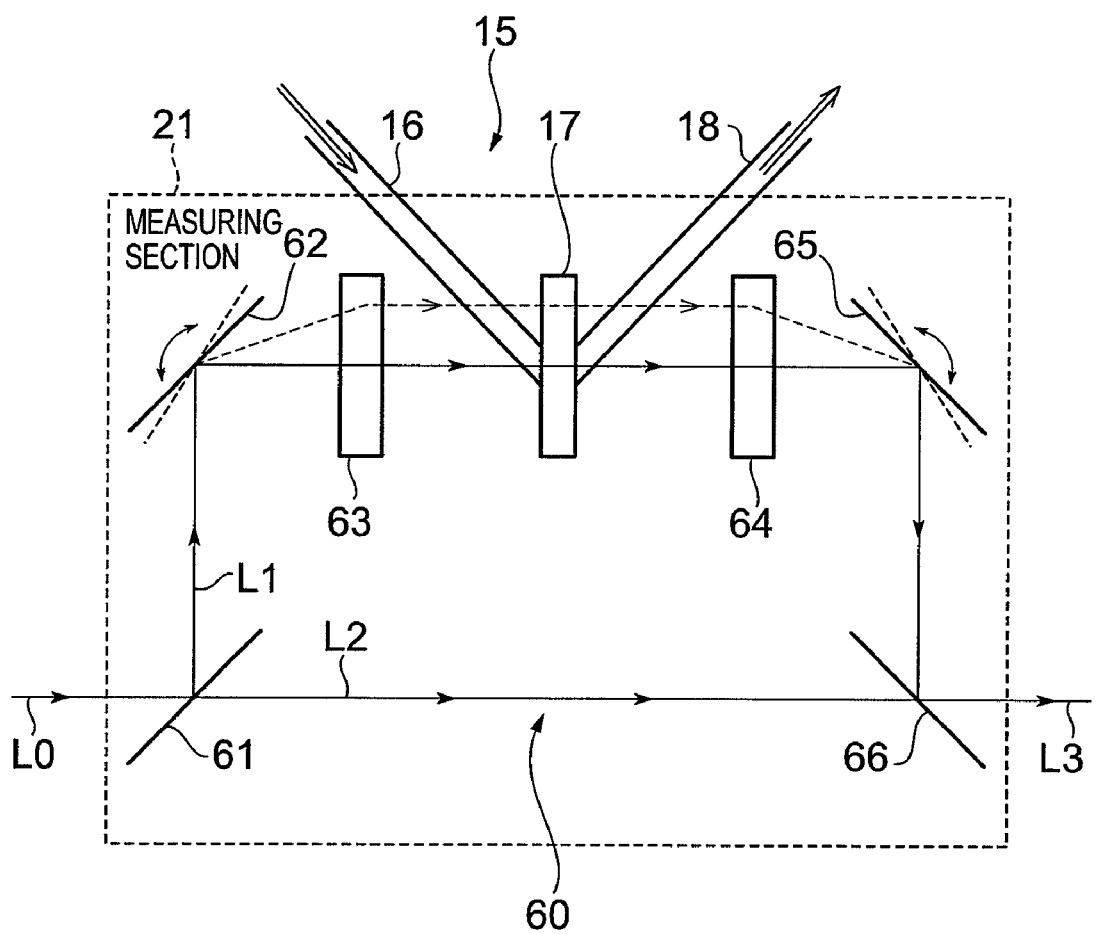
FIG. 3 is a diagram illustrating an example of a constitution of a measuring section in the cell sorting apparatus.

Next, an example of a concrete constitution of the cell sorting apparatus according to the above embodiment will be described. FIG. 3 is a diagram illustrating an example of a constitution of the measuring section 21 in the cell sorting apparatus illustrated in FIG. 1. The measuring section 21 has a flow path system 15, through which blood containing the cells to be measured flows, and an interference optical system 60 for optically measuring the cells in blood.

The flow path system 15 includes an input flow path 16 for introducing blood, which is supplied from the supplying section 14 under a predetermined condition, into the measuring section 21; a flow cell 17 into which blood is introduced through the input flow path 16 and which is used for cell measurement; and an output flow path 18 for outputting blood subjected to cell measurement in the flow cell 17 to the cell separating section 30 of the subsequent stage. In FIG. 3, blood in the flow cell 17 flows in a direction perpendicular to the sheet.

In addition, the interference optical system 60 includes a half mirror 61; a galvano mirror 62; telecentric fθ lenses 63, 64; a galvano mirror 65; and a half mirror 66, in this order from the upstream side. Additionally, in the interference optical system 60, the flow cell 17, through which blood flows, is arranged between the telecentric fθ lenses 63, 64. Moreover, in the case of making the cells flow in a line, it is unnecessary to provide a beam scanning mechanism optical system such as a galvano mirror or telecentric fθ lens.

Measurement light L0 supplied from the measurement light source 22 is branched into two beams by the half mirror 61. In the constitution example shown in FIG. 3, light reflecting on the half mirror 61 corresponds to irradiation light L1 with which the flow cell 17 is irradiated, and light penetrating through the half mirror 61 corresponds to reference light L2 for interference measurement. The reference light L2 does not pass through the flow cell 17 and the like, and goes straight to reach the half mirror 66 of the subsequent stage.

A predetermined region of blood containing the cell flowing through the flow cell 17 is irradiated with the irradiation light L1, as the measurement light, via the galvano mirror 62 and telecentric fθ lens 63. The light passing through the flow cell 17 reaches the half mirror 66 via the telecentric fθ lens 64 and galvano mirror 65. Then, the light L1 reflecting on the half mirror 66 and reference light L2 penetrating through the half mirror 66 interfere with each other to form interference light L3.

The intensity of the interference light L3 is detected by the detector 23, and thus information is acquired regarding presence/absence of a cell in the blood flowing through the flow cell 17 and the physical quantity, for example thickness, relating to the volume of the cell or nucleus of the cell in the case of presence of the cell. In the case of acquiring the interference light intensity as the cell information corresponding to the physical quantity relating to the volume of the cell or nucleus of the cell, for example, a method can be used, the method for setting an intensity threshold as a sorting condition of sorting a specific type of cell and deciding, based on the threshold, whether the cell is the specific type of cell.

Moreover, the interference light intensity has no linear correlation with the phase change quantity. Accordingly, as the need arises, the phase difference quantity may be quantitatively measured with use of a method such as a phase shift method so that the cells are sorted based on a predetermined threshold for the phase difference quantity (see, for example, "K. Creath, "Phase-measurement interferometry techniques" in Progress in Optics Vol. XXVI, E. Wolf, ed., pp. 349-393 (1988)", and Y Zhao, "Phase-resolved optical coherence tomography and optical Doppler tomography for imaging blood flow in human skin with fast scanning speed and high velocity sensitivity", Optics Letter, Vol. 25, No. 2, (2000)). In the case where a phase noise generates a measurement error here, various phase noise offsetting techniques may be used, one of the techniques disclosed in US 2005/0105097A1.

Figure 4:
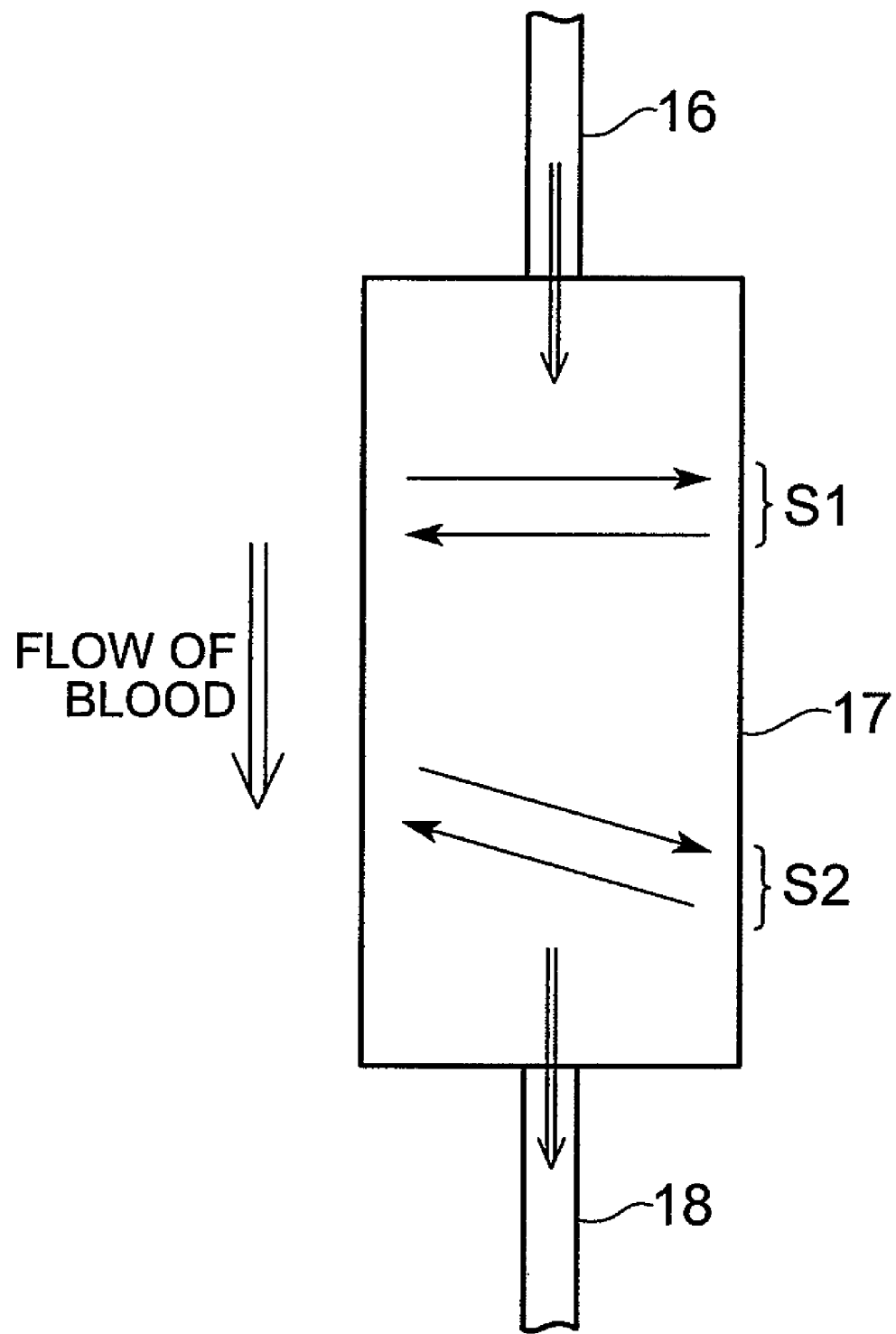
FIG. 4 is a diagram illustrating an example of a constitution of a flow cell used in the measuring section.

FIG. 4 is a diagram illustrating an example of the constitution of the flow cell 17 used in the measuring section 21 illustrated in FIG. 3. As indicated by arrows S1 in FIG. 4, it is preferable that the flow cell 17 is irradiated with the irradiation light (measurement light) L1 while the light moving so as to cross the flow of blood in the flow cell 17 with use of the galvano mirror 62 and telecentric fθ lens 63. Additionally, in the case where the flowing speed of blood is higher than the scanning speed of the irradiation light L1, the irradiation light L1 may be set so as to obliquely move in accordance with the flowing speed as indicated by arrows S2.

Alternatively, a plurality of beams of the irradiation light L1 for scanning the flow cell 17 may be provided. In addition, a plurality of measuring sections 21 may be provided. In this case, throughput of the cell measurement can be improved. Additionally, another galvano mirror may be provided so that the irradiation light L1 is two-dimensionally moved with respect to the scanning surface (flow cell). Further, the reference light L2 may be made to pass through the flow cell 17 under a condition of not passing through the cells. Furthermore, as disclosed in the document, "James F. Leary "Strategies for rare cell detection and isolation", Methods in Cell Biology Vol. 42, pp. 331-358 (1994)", addition of an analog pipe delay, shift register or the like allows, to some extent, dead time to be prevented from lowering the throughput.

Additionally, as for the specific constitution of the interference optical system 60, although a constitution with a Mach-Zehnder interferometer is used in FIG. 3, other constitutions, for example a constitution with a Michelson interferometer, can be used. Additionally, regarding the optical measurement of the cells in the cell measuring section 20, various types of light, for example, fluorescence, reflected light, scattered light, transmitted light, backward scattered light, forward scattered light, side scattered light and the like from the cell, may be used in addition to light passing through a cell, if being capable of extracting the optical characteristic of the cell.

Figure 5:
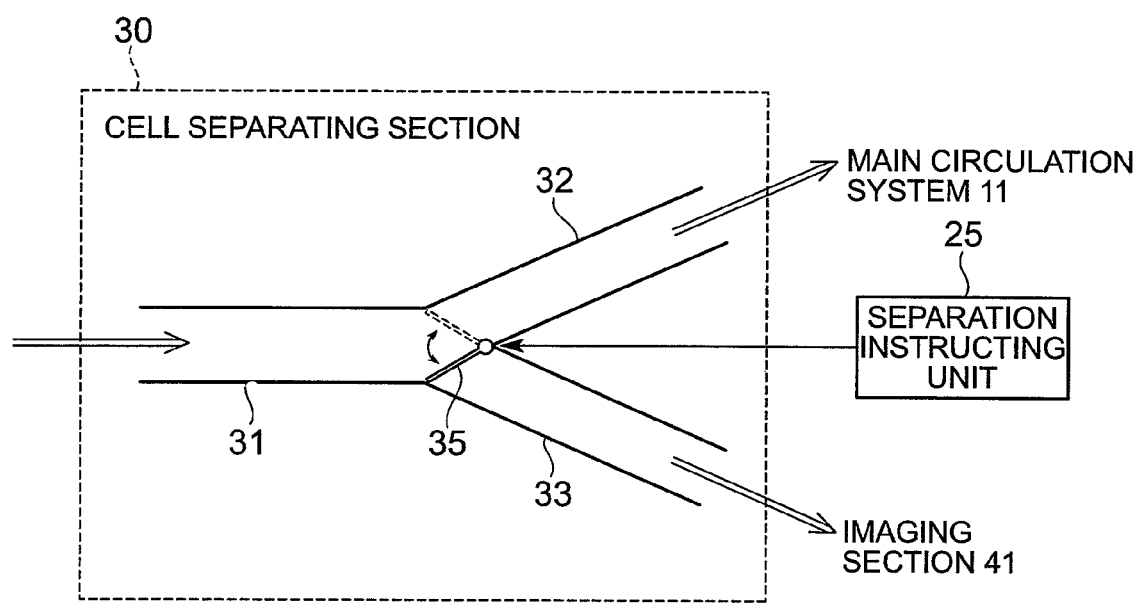
FIG. 5 is a diagram illustrating an example of a constitution of a cell separating section in the cell sorting apparatus.

FIG. 5 is a diagram illustrating an example of a constitution of the cell separating section 30 in the cell sorting apparatus illustrated in FIG. 1. The cell separating section 30 has an input flow path 31, and first output flow path 32 and second output flow path 33, into which the input flow path 31 is branched. Additionally, a separating valve 35 for connecting the input flow path 31 to the output flow path 32 or 33 and separating the cells is provided at a branching point from the input flow path 31 to the output flow paths 32, 33.

The first output flow path 32 is connected to the main circulation system 11 via the flow path 30a, and this flow path 32 is selected in the case where it is decided the cell is not a target cell. Additionally, the second output flow path 33 is connected to the imaging section 41, and this flow path 33 is selected in the case where it is decided the cell is a target cell (for example, cancer cell), and the cell is separated. Additionally, switching operation of the separating valve 35 for switching the flow path is controlled by the separation instructing signal transmitted from the separation instructing unit 25.

Figure 6:
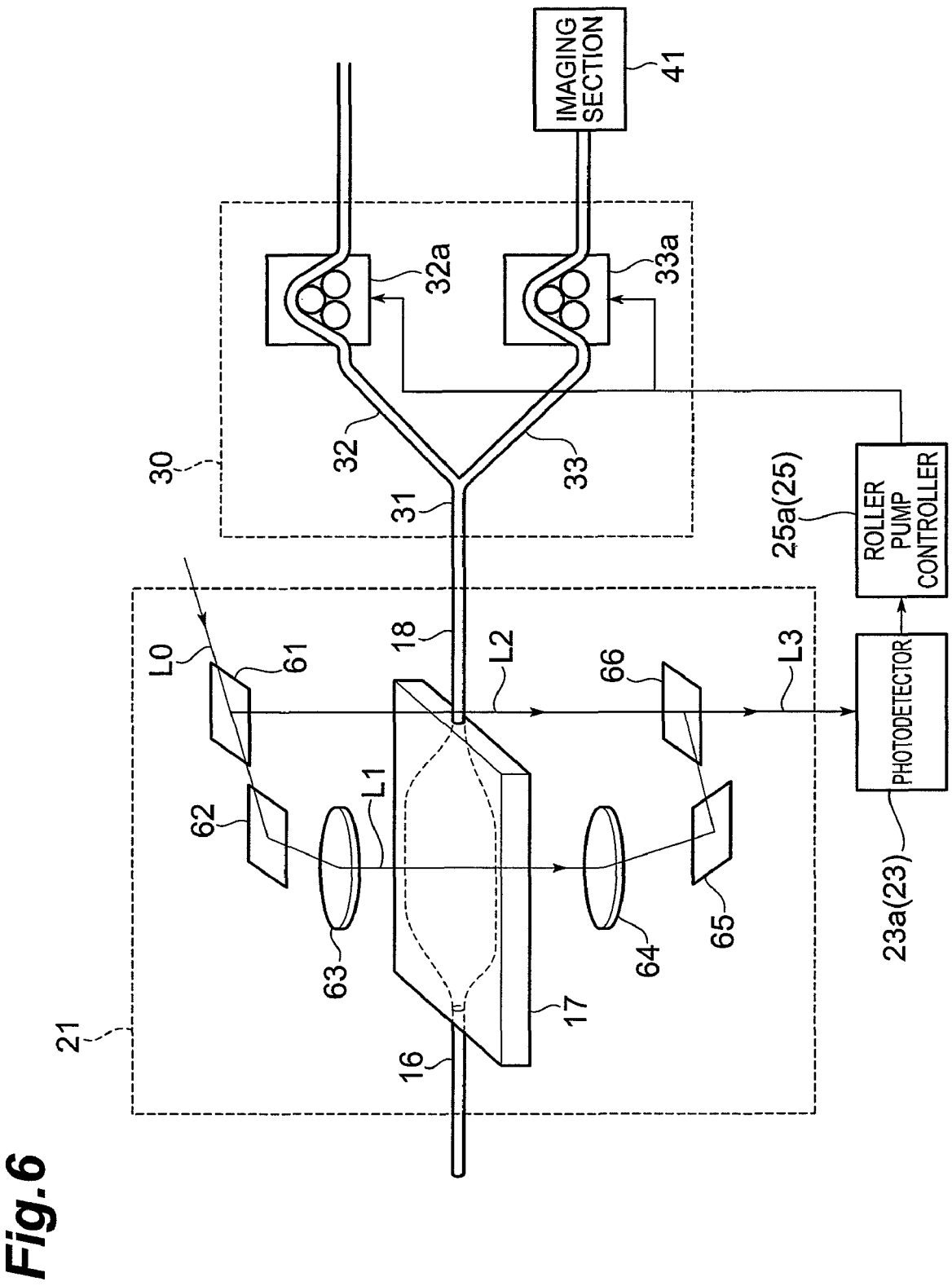
FIG. 6 is a diagram schematically illustrating a concrete constitution example of the measuring section and cell separating section in the cell sorting apparatus.

FIG. 6 is a diagram schematically illustrating another constitution example of the measuring section 21 and cell separating section 30 in the cell sorting apparatus. In this constitution example, the constitution of the measuring section 21 is similar to that illustrated in FIG. 3. Additionally, in the cell separating section 30, roller pumps 32a, 33a are provided for the output flow paths 32, 33, respectively. A detection signal, which is acquired by detecting the interference light L3 by a photodetector 23a of the detector 23, is input into a roller pump controller 25a which is the separation instructing unit 25, and the roller pumps 32a, 33a are drive-controlled by the separation instructing signal from the separation instructing unit 25.

Moreover, as a concrete cell separating method in the cell separating section 30, various methods, for example, a method for forming and charging a liquid drop and separating cells with electrodes, can be adopted in addition to the above-described method. Additionally, methods such as optical tweezers with use of light pressure and sorting with use of an optical lattice (see "Nature Vol. 426, pp. 421-424 (2003)") may be adopted. In the case of using the optical tweezers or optical lattices, the intensity or lattice density of light may be controlled by the separation instructing signal.

Additionally, in the case where the cell group to be sorted is relatively simple, the separation instructing signal is unnecessary, and the sorting is sometimes possible with use of only the optical lattice in a state where the intensity, lattice density or the like is fixed (see "M. P. MacDonald, G. C. Spalding, and K. Dholakia, "Microfluidic sorting in an optical lattice", Nature Vol. 426, pp. 421-424 (2003)"). Such a constitution is a technique for separating the cells based on a difference between optical characteristics of the cells, and simultaneously optically measuring and separating the cells. In this case, the measuring section 21 and the like illustrated in FIG. 1 becomes unnecessary. Generally, in the above cell sorting apparatus, single means serving as both the cell measuring means and cell separating means may be used.

Additionally, the time, when the target cell is detected by the cell measuring section 20 and reaches the cell separating section 30, changes, and a timing of the separation instructing signal sometimes deviates from a timing when the cell reaches the cell separating section 30. In such a case, a margin may be provided in a timely manner for safety and the cells may be separated in a state where non-target cells are mixed with the target cell to some extent.

The cell sorting apparatus of the present invention is not limited to the above embodiments and constitution examples, and can be modified in various ways. For example, although the extracorporeal circulation system 10 for sampling blood from the subject and circulating it includes the main circulation system 11 and bypass circulation system 12 in the constitution illustrated in FIG. 1, an extracorporeal circulation system may be constituted that prepares a shunt similarly to artificial dialysis and directly samples blood outside a body.

The cell sorting apparatus of the above embodiment includes (1) the extracorporeal circulation system for sampling blood from the subject, circulating the blood outside a body and returning the blood into the body; (2) the cell measuring means for supplying the measurement light to the cells contained in the blood sampled by the extracorporeal circulation system to optically measure the cell information on the physical quantity relating to the volume of the cell itself or nucleus of the cell; and (3) the cell separating means for separating, based on the cell information measured by the cell measuring means and sorting condition set for sorting a specific type of cell, cells which satisfy the sorting condition, and returning the other cells into the body via the extracorporeal circulation system.

Here, the sorting apparatus preferably includes separation instructing means for transmitting into the cell separating means the separation instructing signal indicating whether the cell satisfies the sorting condition based on the result of comparison of the cell information measured by the cell measuring means and the sorting condition. Thus, sorting and separating the cells can be securely performed based on the cell information and sorting condition.

Additionally, as a concrete method for acquiring the cell information, a method can be adopted, the method of, in the cell measuring means, irradiating a predetermined region of the blood containing the cell with the measurement light, and setting the phase difference information acquired by detecting the light passing through the cell as the cell information. The phase difference information, which is generated when the measurement light passes through the cell, is thus measured as the physical quantity relating to the volume, and thus the information regarding the volume or thickness of the cell or nucleus of the cell can be suitably acquired without addition of an excess material or the like, the information being necessary for sorting the cells. Additionally, as described below, information other than the phase difference information, for example, scattering intensity information of light, may be optically measured so that the cells are sorted.

Additionally, the sorting apparatus may further include image acquiring means for acquiring an image of the cell separated by the cell separating means as a cell satisfying the sorting condition, in addition to the above cell measuring means and cell separating means. According to such a constitution, the first step of cell sorting is performed with use of the cell information measured by the cell measuring means, the second step of cell sorting is then performed with use of the image acquired by the image acquiring means, and thus the cells can be sorted at high precision. Additionally, since the images of only the cells sorted at the first step are acquired, the memory size necessary for recording images, and time necessary for acquiring images or processing images can be prevented from increasing.

In this case, the sorting apparatus preferably includes displaying means for displaying the image of the cell acquired by the image acquiring means. In such a constitution, the image displayed by the displaying means allows the operator to decide, by visual recognition or the like, whether the cell is the specific type of cell.

Alternatively, the sorting apparatus preferably includes image analyzing means for analyzing the image of the cell acquired by the image acquiring means with reference to the previously prepared information of the specific type of cell and deciding whether the cell is the specific type of cell. In such a constitution, the cell image is analyzed so that it is decided, at high precision and automatically, whether the cell is the specific type of cell.

Additionally, the sorting apparatus preferably includes cell treating means for subjecting the cell, which is decided as the specific type of cell by the image analyzing means, operator or the like, to a predetermined treatment and returning the treated cell into the body via the extracorporeal circulation system. Thus, various operations, for example, selective injection of a medicine into the cancer cells, can be performed. Additionally, in this case, the cell treating means may subject the cell to the homing treatment for making the cell express the homing function of directing the cell to a specific tissue. In this case, for example, the cell expressing the homing function can be used as a conveyer of the medicine.

INDUSTRIAL APPLICABILITY

The present invention can be used as a cell sorting apparatus capable of suitably sorting a target cell from cells in blood.

The invention claimed is:

1. A cell sorting apparatus comprising:
an extracorporeal circulation system for sampling blood from a subject, circulating the blood outside a body and returning the blood into the body;
cell measuring means for supplying measurement light to cells contained in the blood sampled by the extracorporeal circulation system to optically measure cell information on the physical quantity relating to the volume of the cell itself or a nucleus of the cell, such that the cell measuring means irradiates a predetermined region of the blood containing the cell with the measurement light, acquires phase difference information by detecting light passing through the cell, and sets the phase difference information as the cell information;
cell separating means for separating, based on the cell information measured by the cell measuring means and a sorting condition set for sorting a specific type of cell, cells which satisfy the sorting condition to perform a first cell sorting, and returning the other cells into the body via the extracorporeal circulation system;
image acquiring means for acquiring an image of the cell separated by the cell separating means that satisfied the sorting condition; and
image analyzing means for extracting image data of a specific type of cell from the image acquired by the image acquiring means to perform a second cell sorting.

2. The cell sorting apparatus according to claim 1, further comprising separation instructing means for transmitting into the cell separating means a separation instructing signal indicating whether the cell satisfies the sorting condition, based on a result of comparison of the cell information measured by the cell measuring means and the sorting condition.

3. The cell sorting apparatus according to claim 1, further comprising displaying means for displaying an image of the cell acquired by the image acquiring means.

4. The cell sorting apparatus according to claim 1, wherein the image analyzing means further analyzes the image of the cell acquired by the image acquiring means with reference to previously prepared information of the specific type of cell, and deciding whether the cell is the specific type of cell.

5. The cell sorting apparatus according to claim 1, further comprising cell treating means for subjecting the cell, which is decided as the specific type of cell, to a predetermined treatment, and returning the treated cell into the body via the extracorporeal circulation system.

6. The cell sorting apparatus according to claim 5, wherein the cell treating means subjects the cell to homing treatment for making the cell express a homing function of directing the cell to a specific tissue.

* * * * *